United States Patent [19]

Sanchez et al.

[11] Patent Number: 4,950,786

[45] Date of Patent: Aug. 21, 1990

[54] METHOD FOR MAKING 2,6-NAPHTHALENE DICARBOXYLIC ACID

[75] Inventors: Paul A. Sanchez, Burr Ridge; David A. Young, Cresthill; George E. Kuhlmann, Naperville; Walter Partenheimer, Naperville; Wayne P. Schammel, Naperville, all of Ill.

[73] Assignee: Amoco Corporation, Chicago, Ill.

[21] Appl. No.: 350,634

[22] Filed: May 4, 1989

Related U.S. Application Data

[63] Continuation of Ser. No. 145,299, Jan. 19, 1988, abandoned.

[51] Int. Cl.$^5$ .............................. C07C 51/215
[52] U.S. Cl. ....................... 562/416; 560/77; 502/304; 562/412; 562/417; 562/488
[58] Field of Search ............. 562/412, 416, 417, 488; 560/77

[56] References Cited

U.S. PATENT DOCUMENTS

| | | | |
|---|---|---|---|
| 4,709,088 | 11/1987 | Hirose et al. | 562/414 |
| 4,716,245 | 12/1987 | Hirose | 562/416 |
| 4,794,195 | 12/1988 | Hayashi et al. | 562/414 |

FOREIGN PATENT DOCUMENTS 2187744A 9/1987 United Kingdom .

*Primary Examiner*—Werren B. Lone
*Assistant Examiner*—Vera C. Clarke
*Attorney, Agent, or Firm*—James R. Henes; William H. Magidson; Ralph c. Medhurst

[57] ABSTRACT

A method for making 2,6-naphthalene dicarboxylic acid by the oxidation of 2,6-diisopropylnaphthalene or its oxidation derivatives in the presence of a catalyst comprising cobalt, manganese, cerium and bromine components is disclosed.

15 Claims, No Drawings

METHOD FOR MAKING 2,6-NAPHTHALENE DICARBOXYLIC ACID

This is a continuation of application Ser. No. 145,299, filed Jan. 19, 1988, now abandoned.

BACKGROUND OF THE INVENTION

1. Field of the Invention

This invention relates to a method for making 2,6-naphthalene dicarboxylic acid by the oxidation of 2,6-diisopropylnaphthalene or its oxidation derivative with an oxygen-containing gas under liquid-phase conditions and in the presence of a catalyst comprising metal and bromine components.

2. Discussion of the Prior Art

Fibers and films produced from polyethylenenaphthalate have improved strength and thermal properties relative to fibers and films produced from polyethyleneterephthalate and are especially useful in applications such as tire cords, magnetic tape backings and hot-fill containers. However, the use of 2,6-naphthalene dicarboxylic acid is inhibited by its relatively high cost, which is due to the relative unavailability and high cost of the preferred feedstock, 2,6-dimethylnaphthalene, which can be readily oxidized to 2,6-naphthalene dicarboxylic acid under conditions that are conventional for the oxidation of alkylated aromatics—that is, under liquid phase conditions, in a solvent, at elevated temperature and pressure, by an oxygen-containing gas, and in the presence of a catalyst comprising cobalt, manganese and bromine components.

It has been proposed to substitute the more readily available and less expensive 2,6-diisopropylnaphthalene or its oxidation derivative for 2,6-dimethylnaphthalene or its oxidation derivative in the aforesaid conventional oxidation. For example, Hirose et al. (Teijin Petrochemical Industries Ltd.), published European Patent Application No. 142719, disclose that the use of the aforesaid conventional oxidation conditions for the oxidation of 2,6-diisopropylnaphthalene, or its oxidation derivative, results in an extremely low yield of 2,6-naphthalene dicarboxylic acid, which is also of low purity because of the formation of relatively large amounts of undesirable by-products. This published European Patent Application also discloses that variation of the aforesaid conventional oxidation, either by the use therein of a plurality of oxidation stages in which the reaction temperature is increased stepwise or continuously from a relatively low temperature in an early stage to relatively higher temperatures in a latter stage, or by maintaining a low concentration of 2,6-diisopropylnaphthalene or its oxidation derivative in the solvent in the oxidation, did not afford acceptable yields of 2,6-naphthalenedicarboxylic acid.

By contrast, the method of the invention disclosed and claimed in European Patent Application No. 142719 employs a relatively large amount of the aforesaid oxidation catalyst containing a heavy metal element selected from the group consisting of cobalt and manganese and a bromine element, with 0.2 to 10 gram-atoms of the heavy metal element being used per mole of 2,6-diisopropylnaphthalene or its oxidation derivative.

Furthermore, published Japanese patent application Kokai No. 120342/87 discloses a process for oxidizing 2,6-diisopropylnaphthalene or its oxidation derivative to 2,6-naphthalene dicarboxylic acid in a reaction medium containing at least 50 weight percent of propionic acid and in the presence of a catalyst comprising (1) a bromine element, (2) cobalt or manganese or a mixture thereof, and (3) an alkali metal element.

Published Japanese patent application Kokai No. 120343/87 discloses a process that is very similar to that of published Japanese patent application Kokai No. 120342/87 but in which the solvent contains at least 50 weight percent of at least one monocarboxylic acid selected from butyric acid, valeric acid and benzoic acid.

Published Japanese patent application Kokai No. 246143/86 discloses a process that is very similar to that of published Japanese patent application Kokai No. 120342/87 except that at least 70 weight percent of the solvent is acetic acid or propionic acid or a mixture thereof and except that 1.1 to 15 gram atoms of the alkali metal component of the catalyst must be employed per gram atom of the bromine component of the catalyst.

OBJECTS OF THE INVENTION

It is therefore a general object of the present invention to provide an improved method for oxidizing 2,6-diisopropylnaphthalene or its oxidation derivative to 2,6-naphthalene dicarboxylic acid which overcomes the aforementioned problems of the prior art.

More particularly, it is an object of the present invention to provide an improved method for oxidizing 2,6-diisopropylnaphthalene or its oxidation derivative to 2,6-naphthalene dicarboxylic acid with an improved yield of 2,6-naphthalene dicarboxylic acid.

It is another object of the method of the present invention to provide an improved method for oxidizing 2,6-diisopropylnaphthalene or its oxidation derivative to 2,6-naphthalene dicarboxylic acid of improved purity.

Other objects and advantages of the present invention will become apparent upon reading the following detailed description and appended claims.

SUMMARY OF THE INVENTION

These objects are achieved by the improved method of this invention for producing 2,6-naphthalene dicarboxylic acid comprising: exothermically oxidizing 2,6-diisopropylnaphthalene or its oxidation derivative as the starting material with an oxygen-containing gas in the liquid phase in a solvent comprising an aliphatic monocarboxylic acid having, in an oxidation reactor at an elevated temperature and pressure and in the presence of an oxidation catalyst comprising cobalt, manganese, bromine and cerium components, wherein the atom ratio of cobalt (calculated as elemental cobalt) in the cobalt component of the catalyst-to-the starting material is in the range of from about 30 to about 10000 mga per gram mole of the starting material, wherein the atom ratio of manganese (calculated as elemental manganese) in the manganese component of the catalyst-to-cobalt (calculated as elemental cobalt) in the cobalt component of the catalyst is in the range of from about 0.5 to about 3 mga per mga of cobalt, wherein the atom ratio of bromine (calculated as elemental bromine) in the bromine component of the catalyst-to-total cobalt and manganese (calculated as elemental cobalt and elemental manganese) in the cobalt and manganese components of the catalyst is in the range of from about 0.05 to about 1 mga per mga of total cobalt and manganese, wherein the atom ratio of cerium (calculated as elemental cerium) in the cerium component of the catalyst-to-cobalt (calculated as elemental cobalt) in the cerium component of the catalyst is in the range of from about 0.05 to about 1.0 mga per mga of cobalt, and wherein heat generated in the oxidation reactor is at least partially dissipated by vaporization of liquids therein and withdrawal of the resulting vapors from the oxidation reactor and wherein oxygen is maintained at a concentration level in the oxidation reactor such that the concentration of oxygen in the aforesaid withdrawn vapors is in the range of from about 0.1 to about 15 volume percent.

DETAILED DESCRIPTION OF THE PREFERRED EMBODIMENTS

The starting material employed in the method of this invention is represented by the following general formula:

wherein $R_1$ is selected from the group consisting of

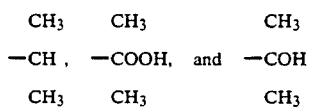

and wherein $R_2$ is selected from the group consisting of

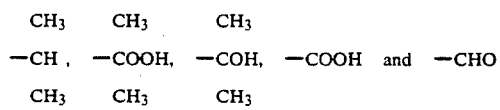

and wherein $R_1$ and $R_2$ can be the same or different from each other. Preferably the starting material is 2,6-diisopropylnaphthalene.

Suitable solvents for use in the method of the present invention for producing 2,6-naphthalene dicarboxylic acid include any aliphatic $C_2$–$C_6$ monocarboxylic acid such as acetic acid, propionic acid, n-butyric acid, isobutyric acid, n-valeric acid, trimethylacetic acid, and caproic acid and mixtures thereof with water. Preferably, the solvent is a mixture of acetic acid and water, which more preferably contains from 1 to 30 weight percent of water and most preferably from 2 to 15 weight percent of water, the total amount of both that introduced into the oxidation reactor from an external source and that generated in situ in the oxidation reaction. Heat generated in the highly exothermic liquid-phase oxidation is dissipated at least partially by vaporization of solvent in the oxidation reactor and withdrawal of at least some of the solvent from the reactor as a vapor, which is then condensed and recycled to the reactor. In addition, some solvent is withdrawn from the reactor as a liquid in the product stream. After separation of the 2,6-naphthalene dicarboxylic acid product from the product stream, at least a portion of the mother liquor (solvent) in the resulting product stream is recycled to the reactor. The weight ratio of the total amount of the monocarboxylic acid solvent (both fresh and recycle)-to-total amount of 2,6-diisopropylnaphthalene added during the entire oxidation step in the method of this invention is from about 2:1, preferably from about 3:1, up to about 20:1, preferably up to about 10:1.

The source of molecular oxygen employed in the method of this invention can vary in molecular oxygen content from that of air to oxygen gas. Air is the preferred source of molecular oxygen. Typically in liquid-phase oxidations of alkylaromatics such as p-xylene by oxygen and in the presence of a catalyst having heavy metal and bromine components, the oxygen-containing gas fed to the reactor provides a pressure of oxygen in the oxidation reactor of from 50 to 300 pounds per square inch gauge and an exhaust gas-vapor mixture containing from 0.5 to 8 volume percent oxygen and preferably from 2 to 6 volume percent oxygen (measured on a solvent-free basis). However, at such levels of oxygen in the method of the present invention, the resulting 2,6-naphthalene dicarboxylic acid product is dark brown. By contrast, preferably in the method of the present invention, the oxygen-containing gas fed to the reactor provides a much higher pressure of from 100 to 500 pounds per square inch gauge and an exhaust gas-vapor mixture containing from 8 to 12 volume percent oxygen (measured on a solvent-free basis). Everything else being equal, at the oxygen levels employed in the method of this invention, the resulting 2,6-naphthalene dicarboxylic acid product is light brown/beige. However, broadly in the method of the present invention, the exhaust gas-vapor mixture contains from 0.1 to 15 volume percent of oxygen.

The catalyst employed in the method of this invention for producing 2,6-naphthalene dicarboxylic acid comprises cobalt, manganese, bromine, and cerium components. The atom ratio of cobalt (calculated as elemental cobalt) in the cobalt component of the catalyst-to-the starting material in the liquid-phase oxidation is in the range of from about 30, preferably from about 60, to about 10000, preferably to about 500, milligram atoms (mga) per gram mole of the starting material. The atom ratio of manganese (calculated as elemental manganese) in the manganese component of the catalyst-to-cobalt (calculated as elemental cobalt) in the cobalt component of the catalyst in the liquid-phase oxidation is in the range of from about 0.5, preferably from about 1.0, to about 3, preferably to about 2.5, mga per mga of cobalt. The atom ratio of bromine (calculated as elemental bromine) in the bromine component of the catalyst-to-total cobalt and manganese (calculated as elemental cobalt and elemental manganese) in the cobalt and manganese components of the catalyst is in the range of from about 0.05, preferably from about 0.075, to about 1, preferably to about 0.4, mga per mga of total cobalt and manganese. The atom ratio of cerium (calculated as elemental cerium) in the cerium component of the catalyst-to-cobalt (calculated as elemental cobalt) in the cobalt component of the catalyst is in the range of from about 0.05, preferably from about 0.1, to about 1.0, preferably to about 0.6, mga per mga of bromine.

One highly preferred embodiment of the oxidation catalyst employed in a preferred embodiment of the method of this invention comprises in addition to the aforesaid cobalt, manganese, bromine and cerium components, a combination of (1) an acetate ion component at a concentration level in the range of from about 3 to about 8, preferably to about 5, mmoles of acetate ion in the acetate ion component of the catalyst per mga of total cobalt and manganese (calculated as elemental cobalt and manganese) in the cobalt and manganese components of the catalyst, and (2) an iron component at a concentration level in the range of from about 0.05, preferably from about 0.1, to about 1.0, preferably to about 0.6, mga of iron (calculated as elemental iron) in the iron component of the catalyst per mmole of cobalt (calculated as elemental cobalt) in the cobalt component of the catalyst.

In an alternative preferred embodiment of the method of this invention, acetic anhydride is also employed at a weight ratio of acetic anhydride-to-the aforesaid organic starting material of from about 1:2, more preferably from about 3:4, to about 4:1, most preferably to about 2:1. In an especially preferred embodiment, the acetic anhydride is added simultaneously with the diisopropylnaphthalene or its oxidation equivalent and semi-continuously as described below.

Each of the cobalt, manganese, bromine, cerium, acetate and iron components can be provided in any of its known ionic or combined forms that provide soluble forms of cobalt, manganese, bromine, cerium, acetate and iron in the solvent in the reactor. For example, when the solvent is an acetic acid medium, cobalt and/or manganese and/or cerium, and/or iron carbonate, acetate, and/or bromide can be employed. The 0.05:1 to 1:1 bromine-to-total cobalt and manganese milligram atom ratio is provided by a suitable source of bromine. Such bromine sources include elemental bromine ($Br_2$), or ionic bromides (for example, HBr, NaBr, KBr, $NH_4Br$, etc.), or organic bromides which are known to provide bromide ions at the operating temperature of the oxidation (e.g., bromobenzenes, benzylbromide, mono- and dibromoacetic acid, bromoacetyl bromide, tetrabromoethane, ethylene-di-bromide, etc.). The total bromine in molecular bromine and ionic bromide is used to determine satisfaction of the elemental bromine-to-total cobalt and manganese milligram atom ratio of 0.05:1 to 1:1. The bromide ion released from the organic bromides at the oxidation operating conditions can be readily determined by known analytical means. Tetrabromoethane, for example, at operating temperatures of 170° to 225° C. has been found to yield about 3 effective gram atoms of bromine per gram mole.

Suitable sources of the acetate ion component of the catalyst employed in the method of this invention include sodium acetate, ammonium acetate, potassium acetate, cesium acetate, lithium acetate, barium acetate, and calcium acetate.

In operation, the minimum pressure at which the oxidation reactor is maintained is that pressure which will maintain a substantial liquid phase of starting material and at least 70 percent of the solvent. When the solvent is an acetic acid-water mixture, suitable reaction gauge pressures in the oxidation reactor are in the range of from about 0 $kg/cm^2$ to about 35 $kg/cm^2$, and typically are in the range of from about 10 $kg/cm^2$ to about 30 $kg/cm^2$. The temperature range within the oxidation reactor is generally from about 150° C., preferably from about 170° C., to about 270° C., preferably to about 200° C. The solvent residence time in the oxidation reactor is generally from about 20 to about 300 minutes and preferably from about 30 to about 180 minutes.

The oxidation of the method of this invention can be performed either on a batch, continuous, or semi-continuous mode. In the batch mode, the starting material, solvent and the catalyst components are initially introduced batchwise into the reactor, and the temperature and pressure of the reactor contents are then raised to the desired levels therefor for the commencement of the oxidation reaction. Air is introduced continuously into the reactor. After commencement of the oxidation reaction—for example, after all of the starting material had been completely introduced into the reactor, the temperature of the reactor contents is raised. In the continuous mode, each of the starting material, air, solvent and the catalyst components dissolved in the solvent are continuously introduced through a first inlet or set of inlets into a first oxidation reactor where the temperature and pressure are at the desired levels therefor for initiation of the oxidation reaction; and a product stream comprising the 2,6-naphthalene dicarboxylic acid product and catalyst components dissolved in the solvent is withdrawn from the reactor. In the semi-continuous mode, the solvent and the catalyst components are initially introduced batchwise into the reactor, and then the starting material and air are introduced continuously into the reactor. After commencement of the oxidation reaction, the temperature of the reactor contents is raised. Typically, the semi-continuous mode is employed for the oxidation of the method of this invention, with the temperature of the reactor contents preferably at about 150°–205° C. when starting material is first introduced and rising to a steady-state temperature of preferably about 170° C.–270° C. as the exothermic oxidation proceeds and with the starting material being introduced preferably at 0.05–1.0 parts per part of solvent by weight per hour preferably for 0.3–4.0 hours.

In each case, the progress of the reaction is monitored by measuring oxygen uptake and temperature changes. A run is terminated after oxygen uptake ceases, as evidenced by a rapid decrease in oxygen uptake—that is, by a rapid increase in the oxygen concentration in the vapor gas mixture withdrawn from the reactor.

Thereafter, the product stream in the continuous mode or the reactor contents in the batch or semi-continuous mode are cooled at a rate of about 25° C.–140° C. per hour to a temperature in the range of from about 35° C. to about 120° C. in at least one step and in at least one crystallizer such that essentially all of the resulting crude, solid 2,6-naphthalene dicarboxylic acid product is separated from the product mixture typically by filtration or centrifugation at a temperature in the range of from about 35° C. to about 120° C. The use of lower temperatures results in the recovery of a significantly less pure product and the use of higher temperatures results in the recovery of less product.

The present invention will be more clearly understood from the following specific examples.

EXAMPLES 1–16

Each of Examples 1–16 involves the oxidation of 2,6-diisopropylnaphthalene on a semi-continuous basis. The reactor employed was a reactor equipped with a stirrer, air line, cooling coil, and a line for introduction of air during the oxidation. In Examples 1–6, a 1-liter reactor was employed, and a 2-liter reactor was employed in Examples 7–16. The temperature of the reactor was controlled by insulated electrical heaters which surrounded the autoclave, and the cooling coil in the reactor. A controlled rate of fluid was passed through the cooling coil during the oxidation. The vented gases from the reactor were passed through a condenser, cooled by dry-ice, and then through instruments which recorded the gaseous flow rate and the concentration of oxygen and carbon oxides in the gas stream. In these examples, an acetic acid solvent (including water added from an external source—that is, in the total of new and recycled solvent—at a concentration based on the acetic acid) and the metal (added in the form of their acetate), and bromine (added as HBr) components of the catalyst were introduced batchwise into the reactor. The reactor was purged and then pressurized to 300 pounds per square inch gauge with a slow addition of nitrogen gas. The temperature of the reactor contents was raised to approximately 170° C., the desired level therefor for commencement of the oxidation, and then 2,6-diisopropylnaphthalene (2,6-DIPN) at a rate of 0.4–0.8 milliliters per minute and air was introduced continuously into the reactor. In Examples 1–13, the 2,6-DIPN introduced continuously was introduced in acetic anhydride; and in Examples 14–16, the 2,6-DIPN introduced continuously was introduced neat. Immediately after the introduction of the 2,6-diisopropylnaphthalene commences, (which required 60–240 minutes in each of Examples 1–16), the temperature of the reactor contents was raised to the reaction temperature, which is given in Table 1. The pressure of the reactor was controlled by a research control valve. The rate of oxidation was determined by measuring the oxygen content of the vent gas and knowing the flow rate of air through the reactor, and was employed as a measure of the extent of conversion of the reactant. The reaction was terminated after oxygen uptake had ceased and the oxygen content of the vent gas exceeded 15 volume percent, whereupon the flow of air into the reactor was replaced by a flow of nitrogen gas into the reactor. The experimental conditions employed in and the results from Examples 1–16 are presented in Table 1. In Table 1, the tailout time represents the time between turning off the 2,6-DIPN feed and turning off the air feed. Furthermore, in Table 1, the initial weight ratio of solvent-to-2,6-DIPN means the ratio of the weight of acetic acid and water added from an external source-to-that of 2,6-DIPN, and the final weight ratio of solvent-to-2,6-DIPN means the weight of acetic acid, acetic anhydride, and water added from an external source-to-the weight of 2,6-DIPN used. Also in Table 1, the yield of 2,6-NDA is measured in two ways: the first is based on the amount of 2,6-naphthalene dicarboxylic acid in the reaction product slurry and reactor wash, and the second is based on the amount of 2,6-naphthalene dicarboxylic acid in the precipitated cake and in the reactor wash. In principle, the yield of 2,6-NDA determined by both measurements should be the same. The yield of TMLA represents the moles of trimellitic acid identified in the reaction product slurry per mole of 2,6-DIPN used.

Comparison of the results in Table 1 for Examples 1 and 2 indicates that the use of a high oxygen partial pressure improves the yield and quality of 2,6-naphthalene dicarboxylic acid (2,6-NDA). Comparison of the results for Examples 2 and 7 with the results of Examples 3 and 8, respectively, indicates that the use of cerium, and in particular at a relatively higher concentration level, in the catalyst affords improved yields of 2,6-NDA. Comparison of the results of Examples 2 and 7 with the results of Examples 4 and 16, respectively, indicates that the use of iron in the catalyst system and acetate ion at a relatively higher concentration level affords improved yields of 2,6-NDA and permits the omission of acetic anhydride from the reaction system. Comparison of the results from Examples 8, 13 and 14 indicates that, when iron is not present in the catalyst system and when acetate ion is not employed at the aforesaid relatively higher concentration level, acetic anhydride must be employed in the reaction system in order to achieve desirable yields and quality for the 2,6-NDA product. Comparison of the results of Examples 5, 6, 7, 8, 11, 12 and 13 indicates that the solvent rates and concentration of acetic anhydride can be reduced without deleteriously affecting the yield or quality of 2,6-NDA product.

From the above description, it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

Having described the invention, what is claimed is:

TABLE I

| Experimental Parameters | Example No. | | | |
|---|---|---|---|---|
| | 1 | 2 | 3 | 4 |
| Catalyst Composition | | | | |
| Co[1] | 0.35 | 0.35 | 0.35 | 0.35 |
| Mn[1] | 0.65 | 0.65 | 0.65 | 0.65 |
| Br[1] | 0.14 | 0.14 | 0.14 | 0.14 |
| Ce[1] | 0 | 0 | 0.078 | 0 |
| Fe[1] | 0 | 0 | 0 | 0.056 |
| Co/2,6-DIPN[2] | 0.13 | 0.13 | 0.13 | 0.13 |
| Mn/Co[3] | 2.0 | 2.0 | 2.0 | 2.0 |
| Br/(Co+Mn)[3] | 0.1 | 0.1 | 0.1 | 0.1 |
| Ce/Co[3] | 0 | 0 | 0.09 | 0 |
| Acetate ion/(Co+Mn)[4] | 2.0 | 2.0 | 2.0 | 4.0 |
| Fe/Co[2] | 0 | 0 | 0 | 0.17 |
| Acetic anhydride/2,6-DIPN[4] | 4.0 | 4.0 | 4.0 | 4.0 |
| 2,6-DIPN addition time (min.) | 113 | 113 | 114 | 114 |
| Tailout time (min.) | 16 | 12 | 9 | 8 |
| Water conc. added (wt. %) | 2.50 | 2.50 | 2.50 | 2.50 |
| Wt. (g) solvent/ Wt. (g) 2,6-DIPN-initial | 11.2 | 11.2 | 11.2 | 11.5 |
| -final | 15.2 | 15.2 | 15.2 | 15.5 |
| Temperature (°C.) | 193 | 193 | 193 | 193 |
| Pressure (psig) | 210 | 400 | 400 | 400 |
| Vent oxygen conc. (vol. %) | 5 | 12 | 11 | 12 |
| Experimental Results | | | | |
| 2,6-NDA yield[5] | 58.3 | 65.1 | 73.8 | 68.0 |
| 2,6-NDA yield[6] | 54.8 | 62.9 | 76.2 | 67.7 |
| TMLA yield[5] | 11.8 | 14.5 | 16.3 | 14.5 |
| 2,6-NDA color | Brown Brown/ | Light Brown/ Tan | Light Brown Tan | Light |

| Experimental Parameters | Example No. | | | |
|---|---|---|---|---|
| | 5 | 6 | 7 | 8 |
| Catalyst Composition | | | | |
| Co[1] | 0.35 | 0.35 | 0.35 | 0.35 |
| Mn[1] | 0.65 | 0.65 | 0.65 | 0.65 |
| Br[1] | 0.14 | 0.15 | 0.14 | 0.14 |
| Ce[1] | 0.068 | 0.069 | 0.078 | 0.233 |
| Fe[1] | 0 | 0 | 0 | 0 |
| Co/2,6-DIPN[2] | 0.13 | 0.09 | 0.13 | 0.13 |
| Mn/Co[3] | 2.0 | 2.0 | 2.0 | 2.0 |
| Br/(Co + Mn)[3] | 0.1 | 0.1 | 0.1 | 0.1 |
| Ce/Co[3] | 0.08 | 0.08 | 0.09 | 0.28 |
| Acetate ion/(Co + Mn)[4] | 2.0 | 2.0 | 2.0 | 2.0 |
| Fe/Co[2] | 0 | 0 | 0 | 0 |
| Acetic anhydride/2,6-DIPN[4] | 4.0 | 4.0 | 4.0 | 4.0 |
| 2,6-DIPN addition time (min.) | 181 | 119 | 119 | 118 |
| Tailout time (min.) | 11 | 9 | 9 | 9 |
| Water conc. added (wt. %) | 2.50 | 2.47 | 2.50 | 2.50 |
| Wt. (g) solvent/ Wt. (g) 2,6-DIPN-initial | 11.2 | 7.9 | 11.2 | 11.2 |
| -final | 15.2 | 11.9 | 15.2 | 15.2 |
| Temperature (°C.) | 193 | 193 | 193 | 193 |
| Pressure (psig) | 450 | 450 | 400 | 400 |
| Vent oxygen conc. (vol. %) | 13 | 14 | 12 | 12 |
| Experimental Results | | | | |
| 2,6-NDA yield[5] | 62.9 | 71.7 | 57.9 | 67.8 |
| 2,6-NDA yield[6] | 61.8 | 71.2 | 56.8 | 68.6 |
| TMLA yield[5] | 16.2 | 17.9 | 12.0 | 11.3 |
| 2,6-NDA color | Light | Light | Light | Light |

TABLE I-continued

| Experimental Parameters | Brown/Tan | Brown/Tan | Brown/Tan | Brown/Tan |
|---|---|---|---|---|
| | \multicolumn{4}{c}{Example No.} | | | |
| | 9 | 10 | 11 | 12 |
| Catalyst Composition | | | | |
| $Co^1$ | 0.35 | 0.17 | 0.35 | 0.35 |
| $Mn^1$ | 0.65 | 0.33 | 0.65 | 0.65 |
| $Br^1$ | 0.14 | 0.14 | 0.14 | 0.14 |
| $Ce^1$ | 0.078 | 0.039 | 0.078 | 0.078 |
| $Fe^1$ | 0.056 | 0 | 0 | 0 |
| Co/2,6-DIPN$^2$ | 0.13 | 0.03 | 0.13 | 0.09 |
| Mn/Co$^3$ | 2.0 | 2.0 | 2.0 | 2.0 |
| Br/(Co + Mn)$^3$ | 0.1 | 0.2 | 0.1 | 0.1 |
| Ce/Co$^3$ | 0.09 | 0.09 | 0.09 | 0.09 |
| Acetate ion/(Co + Mn)$^4$ | 4.0 | 2.0 | 2.0 | 2.0 |
| Fe/Co$^2$ | 0.17 | 0 | 0 | 0 |
| Acetic anhydride/2,6-DIPN$^4$ | 4.0 | 4.0 | 1.0 | 1.0 |
| 2,6-DIPN addition time (min.) | 119 | 119 | 120 | 120 |
| Tailout time (min.) | 7 | 7 | 8 | 7 |
| Water conc. added (wt. %) | 2.50 | 2.6 | 2.50 | 2.50 |
| Wt. (g) solvent/ | | | | |
| Wt. (g) 2,6-DIPN-initial | 11.5 | 5.5 | 11.2 | 7.8 |
| -final | 15.5 | 9.5 | 12.2 | 8.8 |
| Temperature (°C.) | 193 | 196 | 193 | 193 |
| Pressure (psig) | 400 | 400 | 400 | 400 |
| Vent oxygen conc. (vol. %) | 10 | 13 | 12 | 13 |
| Experimental Results | | | | |
| 2,6-NDA yield$^5$ | 68.4 | 46.8 | 67.1 | 65.0 |
| 2,6-NDA yield$^6$ | 66.9 | 45.0 | 65.9 | 64.2 |
| TMLA yield$^5$ | 10.7 | 27.5 | 12.4 | 14.5 |
| 2,6-NDA color | Light Brown | Brown | Light Brown/Tan | Light Brown/Tan |

| Experimental Parameters | 13 | 14 | 15 | 16 |
|---|---|---|---|---|
| | \multicolumn{4}{c}{Example No.} | | | |
| Catalyst Composition | | | | |
| $Co^1$ | 0.35 | 0.35 | 0.35 | 0.35 |
| $Mn^1$ | 0.65 | 0.65 | 0.65 | 0.65 |
| $Br^1$ | 0.14 | 0.14 | 0.14 | 0.14 |
| $Ce^1$ | 0.078 | 0.233 | 0.233 | 0.078 |
| $Fe^1$ | 0 | 0 | 0 | 0.055 |
| Co/2,6-DIPN$^2$ | 0.09 | 0.08 | 0.08 | 0.08 |
| Mn/Co$^3$ | 2.0 | 2.0 | 2.0 | 2.0 |
| Br/(Co + Mn)$^3$ | 0.1 | 0.1 | 0.1 | 0.1 |
| Ce/Co$^3$ | 0.09 | 0.28 | 0.28 | 0.09 |
| Acetate ion/(Co + Mn)$^4$ | 2.0 | 2.0 | 2.0 | 4.0 |
| Fe/Co$^2$ | 0 | 0 | 0 | 0.17 |
| Acetic anhydride/2,6-DIPN$^4$ | 1.0 | 0 | 0 | 0 |
| 2,6-DIPN addition time (min.) | 119 | 74 | 118 | 74 |
| Tailout time (min.) | 5 | 8 | 16 | 8 |
| Water conc. added (wt. %) | 2.50 | 2.50 | 2.50 | 2.50 |
| Wt. (g) solvent/ | | | | |
| Wt. (g) 2,6-DIPN-initial | 7.8 | 6.8 | 6.8 | 7.0 |
| -final | 8.8 | 6.8 | 6.8 | 7.0 |
| Temperature (°C.) | 193 | 193 | 193 | 193 |
| Pressure (psig) | 400 | 400 | 270 | 400 |
| Vent oxygen conc. (vol. %) | 12 | 11 | 7 | 11 |
| Experimental Results | | | | |
| 2,6-NDA yield$^5$ | 72.1 | 45.1 | 57.3 | 57.5 |
| 2,6-NDA yield$^6$ | 72.5 | 44.8 | 56.6 | 59.0 |
| TMLA yield$^5$ | 18.1 | 8.4 | 10.8 | 11.5 |
| 2,6-NDA color | Light Brown/Tan | Light Brown/Tan | Brown | Light Brown |

Footnotes
[1] Weight percent calculated as the respective elemental metal, acetate ion or acetic anhydride and based on the initial solvent weight
[2] Mga of the respective metal, calculated as the elemental metal per mmole of the respective DIPN or acetate ion
[3] Mga of manganese, bromine or cerium, calculated as the element, per mga of cobalt, the total cobalt and manganese, or bromine, respectively, each calculated as the element
[4] Mmoles of the respective acetate ion or acetic anhydride per mga of total cobalt and manganese combined, each calculated as the element, or per mmole of 2,6-DIPN
[5] Mole percent in the total reactor effluent plus reactor wash, based on the moles of 2,6-DIPN
[6] Mole percent in the precipitated cake plus reactor wash, based on the moles of 2,6-DIPN 1. A method for producing 2,6-naphthalene dicarboxylic acid comprising: exothermically oxidizing 2,6-diisopropylnaphthalene or its oxidation derivative as the starting material with an oxygen-containing gas in the liquid phase in a solvent comprising an aliphatic monocarboxylic acid, in an oxidation reactor at an elevated temperature and pressure and in the presence of an oxidation catalyst comprising cobalt, manganese, bromine and cerium components, wherein the atom ratio of cobalt, calculated as elemental cobalt, in the cobalt component of the catalyst-to-the starting material in the liquid-phase oxidation is in the range of from about 30 to about 10000 mga per gram mole of the starting material, wherein the atom ratio of manganese, calculated as elemental manganese, in the manganese component of the catalyst-to-cobalt, calculated as elemental cobalt, in the cobalt component of the catalyst is in the range of from about 0.5 to about 3 mga per mga of cobalt, wherein the atom ratio of bromine, calculated as elemental bromine, in the bromine component of the catalyst-to-total cobalt and manganese, calculated as elemental cobalt and elemental manganese, in the cobalt and manganese components of the catalyst is in the range of from about 0.05 to about 1 mga per mga of total cobalt and manganese, and wherein the atom ratio of cerium, calculated as elemental cerium, in the cerium component of the catalyst-to-cobalt, calculated as elemental cobalt, in the cobalt component of the catalyst is in the range of from about 0.05 to about 1.0 mga per mga of cobalt, wherein heat generated in the oxidation reactor is at least partially dissipated by vaporization of liquids therein and withdrawal of the resulting vapors from the oxidation reactor, and wherein oxygen is maintained at a concentration level in the oxidation reactor such that the concentration of oxygen in the aforesaid withdrawn vapors is in the range of from about 0.1 to about 15 volume percent.

2. The method of claim 1 wherein the atom ratio of cobalt, calculated as elemental cobalt, in the cobalt component of the catalyst-to-the starting material in the liquid-phase oxidation is in the range of from about 60 to about 500 mpa per gram mole of the starting material.

3. The method of claim 1 wherein the atom ratio of manganese, calculated as elemental manganese, in the manganese component of the catalyst-to-cobalt, calculated as elemental cobalt, in the cobalt component of the catalyst is in the range of from about 1.0 to about 2.5 mga per mga of cobalt.

4. The method of claim 2 wherein the atom ratio of bromine, calculated as elemental bromine, in the bromine, calculated as elemental bromine, in the bromine component of the catalyst-to-total cobalt and manganese, calculated as elemental cobalt and elemental manganese, in the cobalt and manganese components of the catalyst is in the range of from about 0.075 to about 0.4 mga per mg of total cobalt and manganese.

5. The method of claim 1 wherein the atom ratio of cerium, calculated as elemental cerium, in the cerium component of the catalyst-to-cobalt, calculated as elemental cobalt, in the cerium component of the catalyst is in the range of from about 0.1 to about 0.6 mga per mga of cobalt.

6. The method of claim 1 wherein the oxygen is maintained at a concentration level in the reactor such that the concentration of oxygen in the withdrawn vapors is in the range of from about 8 to about 12 volume percent.

7. The method of claim 1 wherein the oxidation catalyst additionally comprises an acetate ion component at a concentration level in the range of from about 3 to about 8 moles of acetate ion in the acetate ion component of the catalyst per mga of total cobalt and manganese, calculated as elemental cobalt and elemental manganese, in the cobalt and manganese components of the catalyst, and an iron component at a concentration level in the range of from about 0.05 to about 10 mga of iron, calculated as elemental iron, in the iron component of the catalyst per mmole of cobalt ion in the cobalt ion component of the catalyst.

8. The method of claim 7 wherein the acetate ion component is present in the oxidation catalyst at a concentration level in the range of from about 3 to about 5 moles of acetate ion in the acetate ion component of the catalyst per mga of total cobalt and manganese, calculated as elemental cobalt and elemental manganese, in the cobalt and manganese components of the catalyst, and the iron component is at a concentration level in the range of from about 0.1 to about 0.6 mga of iron, calculated as elemental iron, in the iron component of the catalyst per mole of cobalt in the cobalt component of the catalyst.

9. The method of claim 1 wherein acetic anhydride is present at a concentration level of from about 50 to about 400 weight percent of the starting material.

10. The method of claim 9 wherein acetic anhydride is at a concentration of from about 75 to about 200 weight percent of the starting material.

11. The method of claim 1 wherein the oxidation is performed at a temperature in the range of from about 150° C. to about 270° C.

12. The method of claim 10 wherein the oxidation is performed at a temperature in the range of from about 170° C. to about 200° C.

13. The method of claim 1 wherein the solvent is a mixture of acetic acid and from about 1 to about 30 weight percent of water, based on the weight of acetic acid.

14. The method of claim 13 wherein the solvent is a mixture of acetic acid and from about 2 to about 15 weight percent of water, based on the weight of acetic acid.

15. The method of claim 1 wherein the pressure is in the range of from about 10 to about 30 kg/cm$^2$ gauge.

* * * * *

UNITED STATES PATENT OFFICE
CERTIFICATE OF CORRECTION

Patent No. 4,950,786          Dated August 21, 1990

Inventor(s) P.A. Sanchez, D.A. Young, G.E. Kuhlmann, W. Partenheimer and W. P. Schammel It is certified that error appears in the above-identified patent and that said Letters Patent is hereby corrected as shown below:

<u>Col.</u>  <u>Line</u>

| Col. | Line | |
|---|---|---|
| 6 | 27 | "preferablY" should read --preferably-- |
| 6 | 36 | "C.-140°" should read --C-140°-- |
| 8 | 42-43 | "Brown Brown/" should read --Brown-- |
| 8 | 42-44 | "Light Brown Tan" should read --Light Brown/Tan-- |
| 8 | 42 | "Light" should read --Light Brown-- |
| 10 | 56 | "mga per mg" should read --mga per mga-- |

Signed and Sealed this

Thirty-first Day of March, 1992

Attest:

HARRY F. MANBECK, JR.

Attesting Officer          Commissioner of Patents and Trademarks